United States Patent [19]

Knap

[11] Patent Number: 4,681,539

[45] Date of Patent: Jul. 21, 1987

[54] DENTAL ARTICULATOR AND METHOD

[76] Inventor: Florian J. Knap, 3000 Mount Hill Dr., Midlothian, Va. 23113

[21] Appl. No.: 773,035

[22] Filed: Sep. 6, 1985

[51] Int. Cl.$^4$ ............................................. A61C 19/04
[52] U.S. Cl. ......................................................... 433/73
[58] Field of Search ............................................ 433/73

[56]  References Cited

U.S. PATENT DOCUMENTS 3,452,439  7/1969  Lee ........................................ 433/36
3,482,312  12/1969  Smith ................................... 433/73
4,368,041  1/1983  Roup ..................................... 433/73

Primary Examiner—Robert Peshock
Attorney, Agent, or Firm—Norman B. Rainer

[57]  ABSTRACT

A method and apparatus for recording condylar motion and utilizing such recording in a dental articulator involves the production of three-dimensional solid recordings formed by the patient executing full mandibular motion, and transferring the recordings under conditions of accurate alignment to a dental articulator where they function as bearing surfaces for the precise reproduction of condylar motion.

10 Claims, 17 Drawing Figures

DENTAL ARTICULATOR AND METHOD

BACKGROUND OF THE INVENTION

This invention relates generally to a dental articulator, and more particularly to improvements in the coupling portions of the articulator and to a method for achieving said improvements.

Attempts to develop useful instrumentation to follow mandibular movements through all its positions and excursions are manifold. The movements of the mandible are three dimensional with right and left articular elements performing similar or dissimilar movement depending on anatomical form and the functions performed. Since the two joints are interconnected, movement in one joint will have an effect on its counterpart.

The chief determinants for rebuilding the patient's occlusion with fidelity are the recording and transferring of the motions of the mandible from the patient to the dental articulator used in such rebuilding.

Dental articulators fall into five general categories according to the function:
 a. Simple hinge which opens and closes.
 b. Semi-adjustable which hinges and also performs protrusive and lateral movements which are guided by average settings.
 c. Adjustable articulators which utilize intra-oral positional jaw records from the patient in centric and eccentric positions to set straight line guiding surfaces or cams in the articulator.
 d. Adjustable articulators with extra-oral pantographic tracings in which the entire tracings are used to set the appropriate articulator.
 e. Adjustable articulator utilizing intra-oral molded pathways which are then transferred to an articulator by molding condylar pathways in the articulator.

The aforementioned earlier methods are faulty either in their inability to capture the three dimensional aspects in recording the data, or in the manipulative difficulties with the articulator's acceptance of the records, or in the transfer of the patient's dental models to the articulator in proper three dimensional orientation to the records. The customized analogs, however, give a closer approximation to the action of the patient's own mandibular joints than do the mechanically adjustable joints or those with average settings.

It is accordingly an object of the present invention to provide an improved, customized analog of reproducing the action of a dental patient's temporomandibular joints.

It is another object of this invention to provide an analog customized for an individual dental patient which may be readily and simply assembled as a dental articulator to reproduce the motion of the patient's temporomandibular joints.

Another object of this invention is to provide an improved method of forming an accurate analog of a dental patient's temporomandibular joint.

A further object of the present invention is to provide a method an apparatus for forming an analog of a temporomandibular joint and accurately relating the patient's dental working model in the assembly of the dental articulator.

These objects and other objects and advantages of the invention will be apparent from the following description.

SUMMARY OF THE INVENTION

The above and other beneficial objects and advantages are accomplished in accordance with the present invention by a method and associated apparatus which construct monolithic three-dimensional bearing surfaces representing condylar pathways, and pivotably mount said surfaces upon stationary upright condyle balls in a dental articulator.

The apparatus is comprised of: (1) a maxillary recording assembly adapted to attach to the upper jaw, (2) a mandibular recording assembly adapted to attach to the lower jaw, (3) an upper articulator member, and (4) a lower articulator member adapted to pivotably engage said upper articulator member.

The maxillary recording assembly is comprised of a first rigid U-shaped bow having a straight forward bar and two extremities positioned at equal distances rearwardly of said forward bar, box-like receptacles removably attached to said rearward extremities, and an upper bite plate (also known as a clutch) pendantly attached to said forward bar and displaced rearwardly therefrom.

The mandibular recording assembly, adapted to be positioned beneath said maxillary assembly, is comprised of a second rigid U-shaped bow having a straight forward bar and extremities provided with posts perpendicularly adjustable with respect to said bow, said posts having affixed to their upper extremities a Teflon ball adapted to enter the receptacles of said maxillary assembly. A lower bit plate or clutch is attached to said forward bar in substantially coplanar relationship therewith and extending rearwardly therefrom to a position of vertical alignment with said upper bite plate.

The upper articulator member is comprised of a rigid plate having a centered aperture, equal left and right side arms radiating away from said aperture in a straight line path, and an arm extending forwardly of said aperture in perpendicular disposition to said side arms. A mounting ring is held to the underside of the plate by a threaded bolt that penetrates said aperture. The distal extremity of said forwardly directed arm holds a vertically adjustable post. The distal extemities of each side arms are provided with means which permit accurate attachment of the aforesaid receptacles.

The lower articulator member is comprised of a horizontally disposed floor plate, a main cross bar supported above the rear extremity of the plate which accommodates vertically positionable left and right Teflon balls adapted to enter the receptacles attached to the upper articulator member, a centrally located threadably attached mounting ring, and an incisal guide table positioned atop the plate adjacent its forward extremity.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

Figure 7:
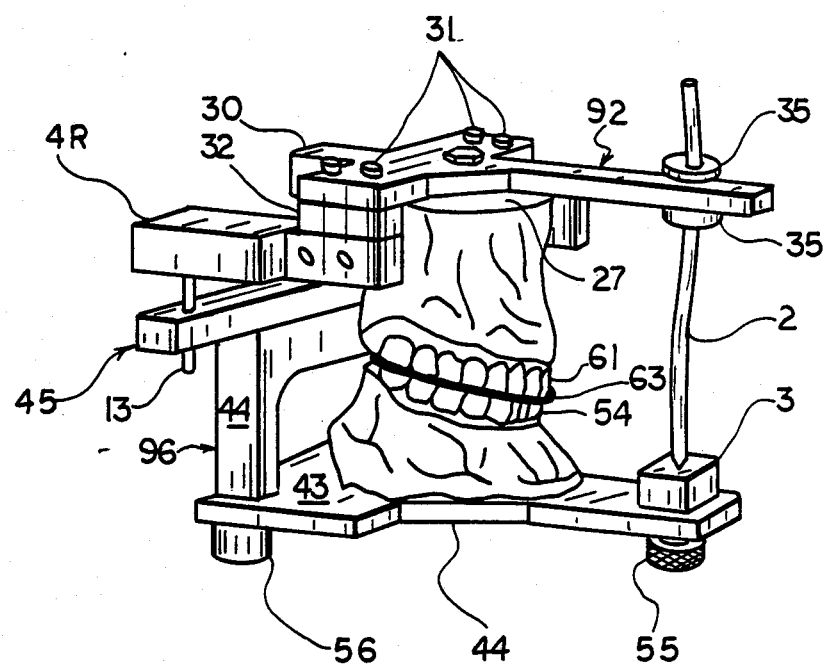
FIG. 7 is a side perspective view of the assembled upper and lower articulator members in association with models of the patient's teeth.

For convenience in description, the terms "front" and "rear", and words of similar import, will have reference to the right and left extremities, respectively, of the apparatus as shown in FIG. 7. Similarly, the terms "left" and "right" will have reference to the left and right portions, respectively, of the component of the apparatus illustrated in FIG. 4A and components suitably oriented thereto. The expression "interior" or equivalents thereof will in general have reference to the geometric center of the apparatus shown in FIG. 7.

DESCRIPTION OF THE PREFERRED EMBODIMENT

Referring to FIGS. 1A, 1B, 1C and 3A, 3B, 3C of the drawing, the maxillary recording assembly 64 is shown comprised of a substantially U-shaped first rigid bow 5 having a straight forward bar 65, and two extremities 66 positioned equidistantly rearwardly of said forward bar. The bow is bounded at its top, bottom, exterior edge and interior edge by substantially flat surfaces 67, 68, 69 and 70, respectively. Shoulders 76 protrude inwardly from interior edge 70 adjacent extremities 66.

Left and right box-like receptacles 4L and 4R, respectively, are securely but removably fastened to the extremities of bow 5. Each receptacle is comprised of a flat upper surface 71, a flat lower surface 72 surrounding a recessed molding cavity 59, flat sidewall edges 73, and an attachment arm 74. The receptacles are attached to bow 5 by means of cap screws 7 which penetrate holes provided in the bow and engage threaded holes 6 in attachment arm 74. In such position of attachment, it is to be noted that the attachment arm 74 is in abutment with the interior edge 70 and shoulder 76 of the bow. When ready for use in recording a patient's condylar pathways, the cavity 59 of each receptacle is filled with a plastic non-elastic recording clay composition capable of being hardened with minimal dimensional change. Suitable compositions include monomers and prepolymers capable of undergoing additional-type polymerization in the presence of catalytic species to form solid products. Such compositions, generally referred to as auto-polymerizing materials, may for example contain cyanoacrylate substances polymerizable by peroxide-type free radical catalysts. Such compositions may also incorporate solid powder lubricants such as Teflon, graphite, talc and molybdenum disulfide. In some embodiments, thin plates 23 as shown in FIG. 3C, containing a circular indentation 77, may be placed within the molding cavity, their presence being useful as positioning guides for the subsequent recording step. An orientation pointer 8 of threadably adjustable length may be removably associated with the interiorly directed portion of the sidewall edge 73 of each receptacle, said pointers being directed toward the interior of the bow, and used to position the apparatus upon the patient relative to the patients mandibular condyles. A hardened composition having a condylar tracing or pathway 60 is shown filling one cavity 59 in FIG. 3C.

An upper bite plate 9, also known as a maxillary clutch, is pendantly attached to forward bar 65 by a slidable fastener 11 and post 10 depending therefrom. Movement of fastener 11 upon bar 65 is controlled by set screw 78. A support bar 79 extends connectively between the lowermost extemity of post 10 and maxillary clutch 9. Such arrangement of components allows for positioning of the maxillary recording bow in horizontal alignment with the midline of the face and vertically aligned with the Frankfort Plane (axis orbital plane). Said maxillary clutch is upwardly and reardwardly domed. A trough 80 extends about the front and sides of the upper surface of the clutch, said trough being adapted to receive a material such as a paste of zinc oxide and eugenol which forms maxillary tooth imprint 62. The underside of the maxillary clutch is comprised of a forwardly disposed upwardly curved bearing surface 57 and opposed substantially flat side portion 58.

The mandibular recording assembly 81, as shown in FIGS. 2A, 2B, 2C and 2D, is comprised of second rigid U-shaped bow 12 having straight forward bar 82, and rearwardly disposed extremities 83. The bow is bounded at its top, bottom, exterior edge and interior edge by substantially flat surfaces 84, 85, 86 and 87, respectively. A smooth bore circular cylindrical channel 88 is perpendicularly disposed to said top and bottom surfaces adjacent extremities 83. A cylindrical post 13 is adapted to slidably engage channel 88. The uppermost extremity of said post, located above top surface 84, is provided with an attached ball 14, preferably fabricated of Teflon material. The position of the ball above said top surface is fixed by cap screw 16 which penetratively engages a threaded channel communicating horizontally between outside surface 86 and channel 88. The balls are spaced in a manner to enter the respective receptacles of the overlying maxillary recording assembly.

A lower bite plate or clutch 19 is attached by extension bar 21 and slidable fastener 22 to forward bar 82 in substantially coplanar relationship therewith and extending rearwardly therefrom to a position of vertical alignment with said upper bite plate. The underside of bite plate 19 is provided with a U-shaped trough 100 adapted to receive an imprint paste such as that used in upper bite plate 9. A vertically adjustable bearing stud 20, extending upwardly from the substantially flat upper surface 89 of said bite plate, is centered within the sagittal plane represented by dashed line 90, and is adapted to engage the curved forward bearing surface 57 of said upper bite plate. An L-shaped guide pin 17 is slidably engaged by channel 91 in close parallel juxtaposition to channel 88. A threaded lock bolt 18 penetrates an edge of the bow to fix the position of pin 17 within its channel. The function of guide pins 17 as to aid in the proper positioning of balls 14 when the receptacles are filled with the recording material.

Figure 4A:
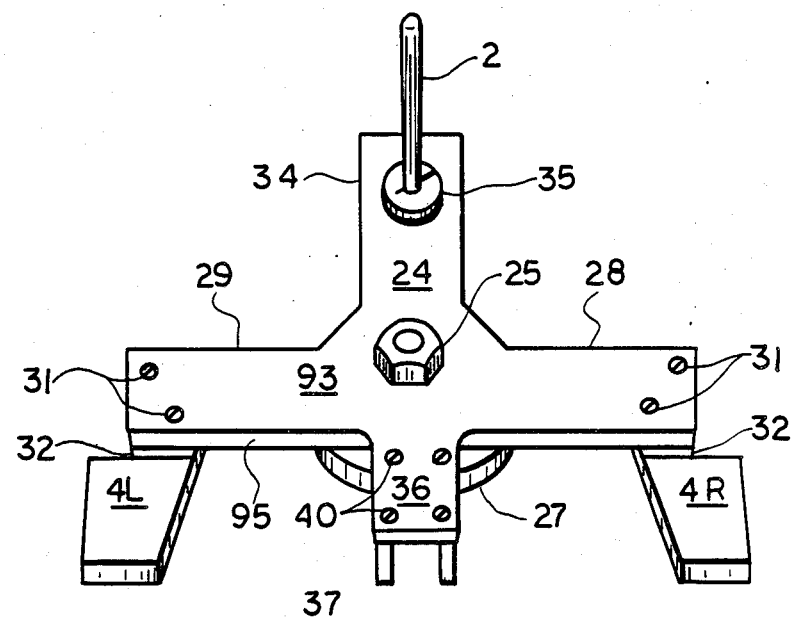
FIG. 4A is a top perspective view of an embodiment of an upper articulator member of the present invention.
Figure 4B:
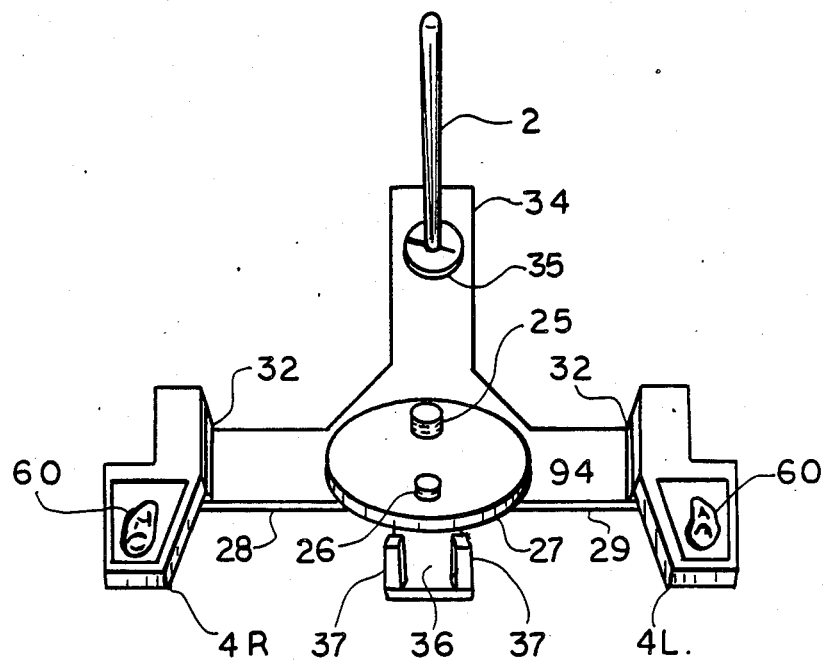
FIG. 4B is a bottom perspective view of the articulator member of FIG. 4A.
Figure 5A:
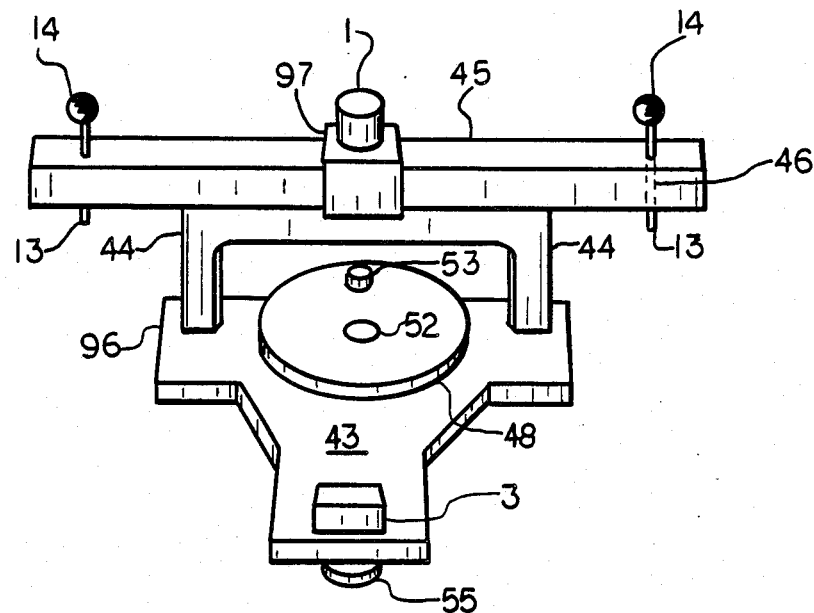
FIG. 5A is a bottom perspective view of an embodiment of the lower articulator member of this invention.
Figure 5B:
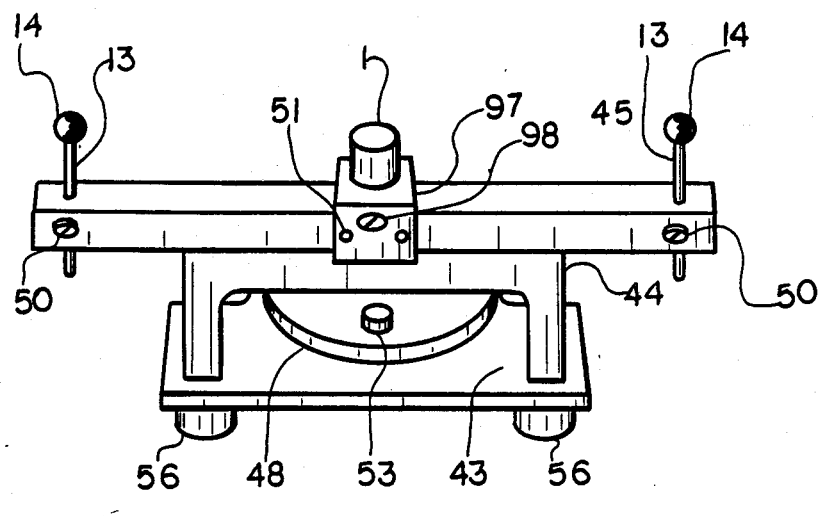
FIG. 5B is a rear perspective view of the articulator member of FIG. 5A.
Figure 5C:
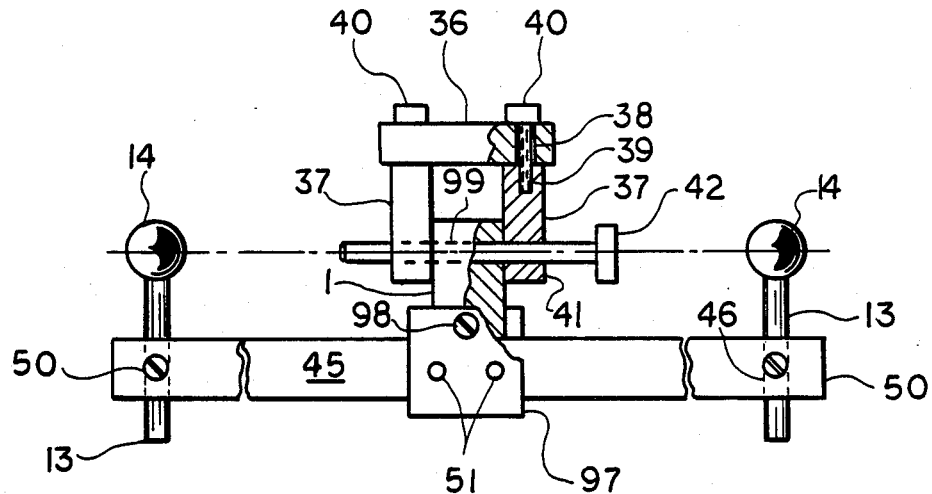
FIG. 5C is a fragmentary rear view of the assembled upper and lower articulator members showing an optional centric lock mechanism.
Figure 6:
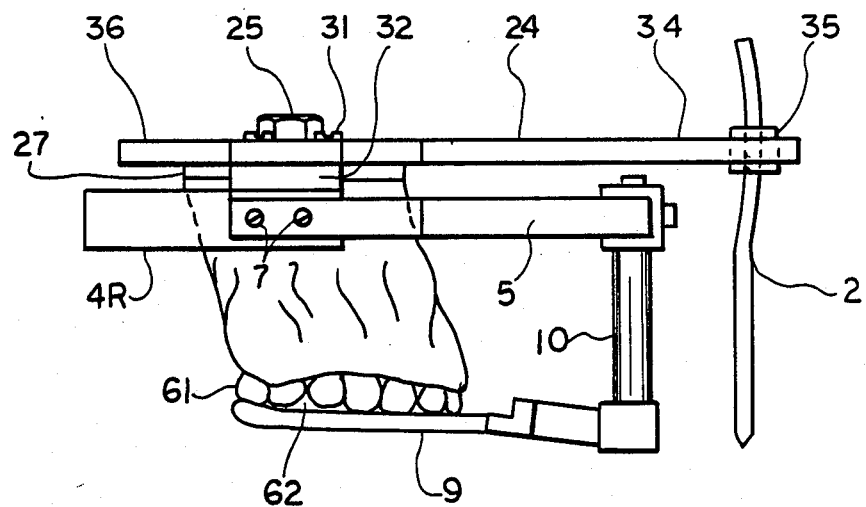
FIG. 6 is a side view showing the manner of transitory interengagement of the maxillary recording assembly with the upper articulator member.

Upper articulator member 92, as shown in FIGS. 4A, 4B and 7, is comprised of rigid base plate 24 having flat upper and lower surfaces 93 and 94, respectively, a boundary sidewall 95, and a penetrating bolt 25 centered in said sagittal plane and extending beneath lower surface 94 and perpendicular thereto. Opposed equal right and left side arm portions 28 and 29, respectively, extend away from the sagittal plane in a straight line path. A forward arm portion 34 extends from said bolt in centered relationship to the sagittal plane and in perpendicular disposition to said side arm portions. A mounting ring 27 is held tightly to lower surface 94 by bolt 25. The forwardmost or distal extremity of arm 34 holds vertically adjustable post 2 whose position is locked by constricting collars 35 or equivalent means.

The distal extremities of side arms 28 and 29 are provided with penetrative threaded bolts 31 adapted to extend below lower surface 94 and into engagement with holes 22 in upper surface 71 of attachment arm 74 of the corresponding receptacles 4L and 4R. In some instances, a spacer block 32 may be inserted between the lower surface of the side arm portions and the underlying receptacle to provide adequate space for mounting the patient's maxillary model. By virtue of the aforesaid arrangement of components, the receptacles are adapted to the transposed from the maxillary recording assembly into the upper articulator member; and during said transposition the receptacles are secured to both the maxillary recording assembly and upper articulator member. Base plate 24 of said upper articulator member may be further provided with a rear extension 36, the underside of which supports paired pivot plates 37 held by bolts 40 which extend through channels 38 and into threaded recesses 39.

Lower articulator member 96, as shown in FIGS. 5A, 5B, 5C, and 7, is comprised of horizontally disposed floor plate 43, the underside of which is provided with one forward and two rearward adjustable bolt footings 55 and 56, respectively. Posts 44 support main cross bar 45 above the rear of said floor plate in parallel relationship therewith and perpendicularly disposed to the sagittal plane. Left and right balls 14 atop posts 13 are vertically positionable above cross bar 45 by virtue of sliding engagement of posts 13 within close-fitting channels 46. Set screws 50 lock posts 13 within channels 46. Said post and ball combinations are preferably identical to those earlier described with respect to mandibular recording assembly 81. The lateral and vertical positioning of the balls is such as to facilitate engagement with condylar moulded pathways 60 within overlying cavities 59.

A lower mounting ring 48 is held fast upon the upper surface of floor plate 43 by centered mounting bolt 52 acting from the underside of said floor plate. Said mounting ring facilitates attachment of the patient's mandibular model 54 as shown in FIG. 7. A positioning stud 53, rising upwardly from said floor plate, engages mounting ring 48 to ensure precise positioning of the ring and model 54 mounted thereupon. An upraised platform 3 having a flat upper surface is positioned upon floor plate 43 adjacent its forward extremity. The upper surface of said platform serves as abutment means for the lowermost extremity of adjustable post 2 of said upper articulator, as shown in FIG. 7. The upper surface of the platform may alternatively be contoured to have angular indentations or a custom molded configuration produced from a clay-like composition comprised of autopolymerizing resin. It is to be noted that the upper extremity of post 2 is shown to have a curvature representing an arc of a circle centered upon a line drawn between the centers of balls 14. Such configuration ensures that, despite vertical adjustments of the post, its lowermost extremity will remain in the same position upon said platform.

A pivot post 1 is rotatably held by bearing block 97 slideably positioned upon cross bar 45. The rotative position of the post is fixed by set screw 98. Movement of the bearing block along cross bar 45 is fixed by set screws 51. The pivot post is adapted to be embraced by pivot plates 37 pendant from the upper articulator member.

A channel 99 penetrates said pivot post in a horizontal direction at a height above said cross bar defined by a line drawn between the centers of the balls. A pivot pin 42 removably extends through said pivot plates and the channel in said pivot post. Such assembly constitutes optional means for pivotably interengaging the upper and lower articulator members so that movement of the upper member toward or away from the lower member is restricted to motion in a vertical path. The pivotal plates 37 are secured to plate 36 in their rearmost part so that they may be loosened and turned out of functional use subsequent to removal of axis pin 42.

In the method of this invention, the maxillary and mandibular clutches 9 and 19, respectively, are fabricated either intraorally or on a conventional hinge type articulator. The facing surfaces of the clutches are adjusted and polished so that bearing post 20 contacts the curved forward portion of the underside of the maxillary clutch, and the peripheral areas of the facing surfaces have smooth simultaneous contact, thereby preventing rocking of the clutches about the bearing post.

The bows are positioned so that balls 14 are seated within the depressions 77 of plates 23 located within cavities 59. The positions of the balls are then adjusted such that there will be no contact with the cavity walls in all possible movements. In such positioning adjustments pointers 8 may be used to secure precise orientation with the condyle axes, thereby providing greater fidelity of the molded pathways to the actual movements of the patient's condyles. Plates 23 and said pointers are then removed, and the cavities are filled with recording clay. The clutches are then cemented to the maxillary and mandibular teeth of the patient using a paste of zinc oxide and eugenol.

The balls are manually seated into the cavities 59 filled with the aforesaid hardenable clay-like plastic composition until the original preclay position of the Teflon balls is achieved. Said preclay position is located using the L-shaped pins 17 located on the mandibular bow, said pins functioning as depth gauges. The balls, now in contact with the plastic composition, function as forming balls.

Figure 1A:
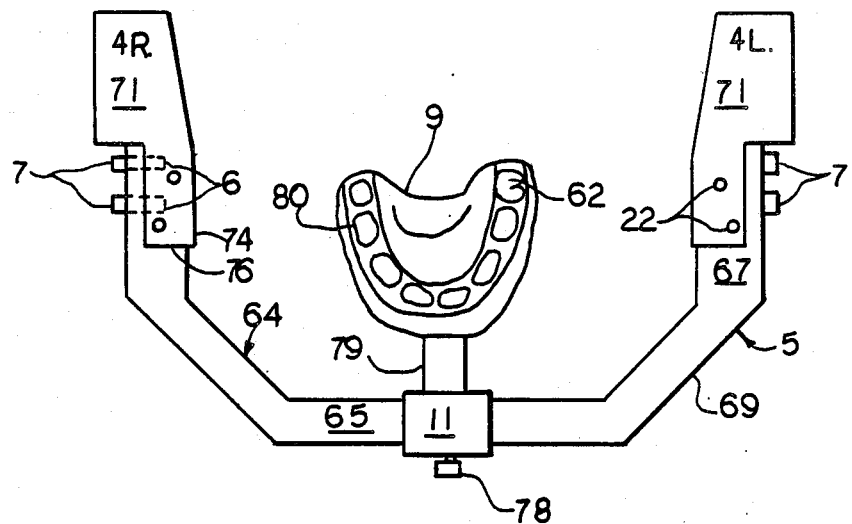
FIG. 1A is a top plan view of an embodiment of the maxillary recording assembly of this invention.
Figure 1B:
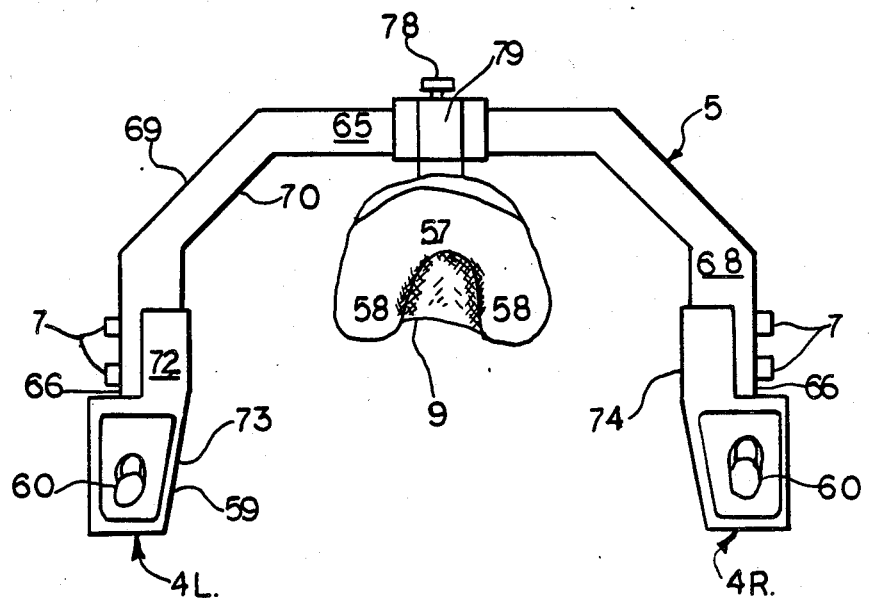
FIG. 1B is a bottom view of the maxillary recording assembly of FIG. 1A.
Figure 1C:
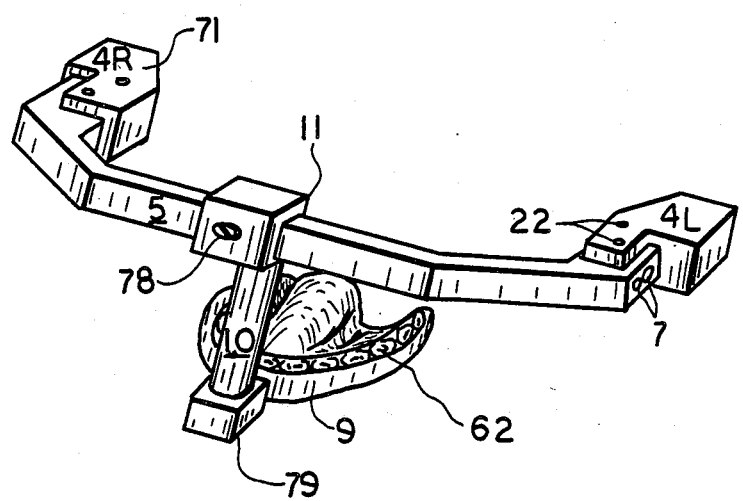
FIG. 1C is a front perspective view of the maxillary recording assembly of FIG. 1A.
Figure 2A:
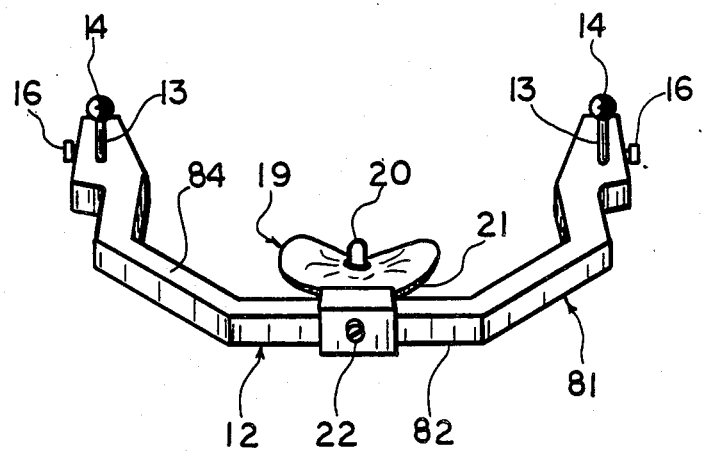
FIG. 2A is a front perspective view of an embodiment of the mandibular recording assembly of this invention.
Figure 2B:
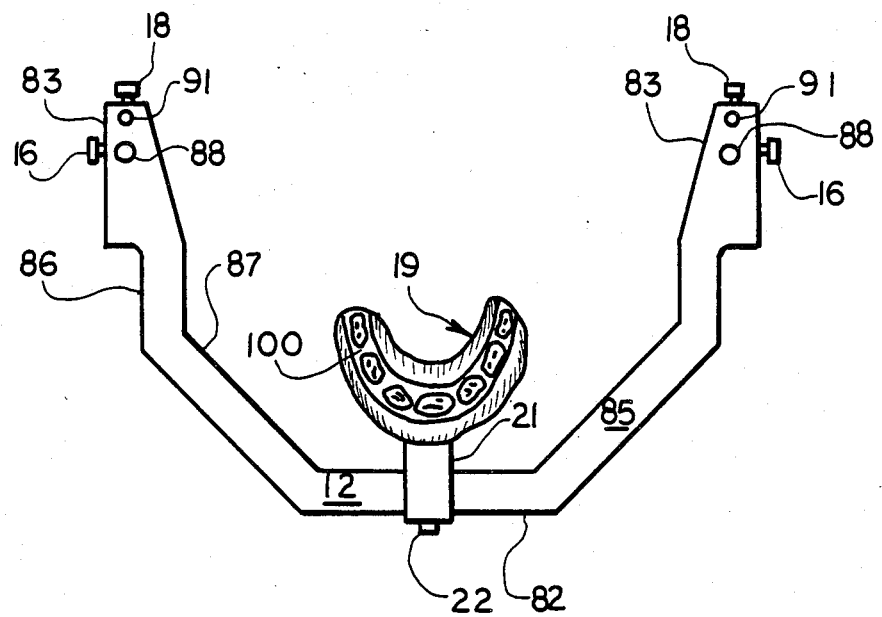
FIG. 2B is a bottom view of the mandibular recording assembly of FIG. 2A.
Figure 2C:
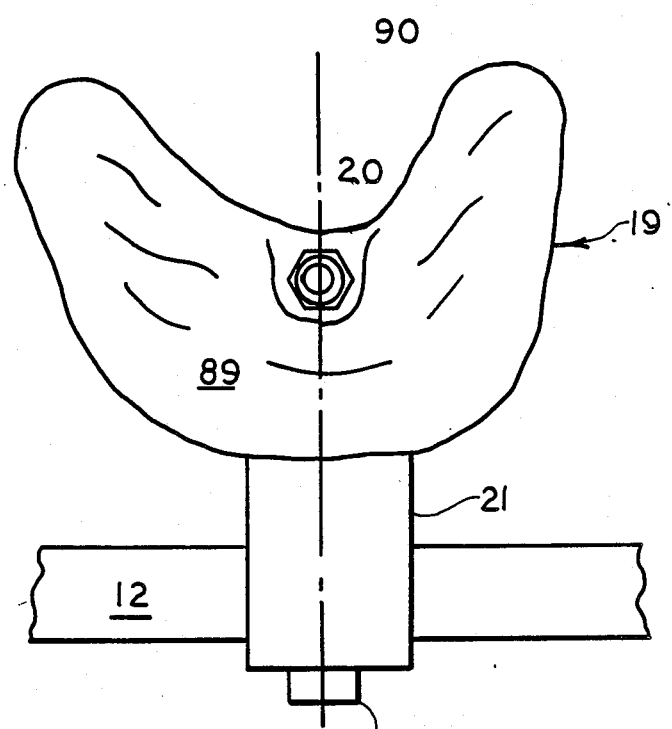
FIG. 2C is an enlarged top view of the lower bite plate shown in FIG. 2A.
Figure 2D:
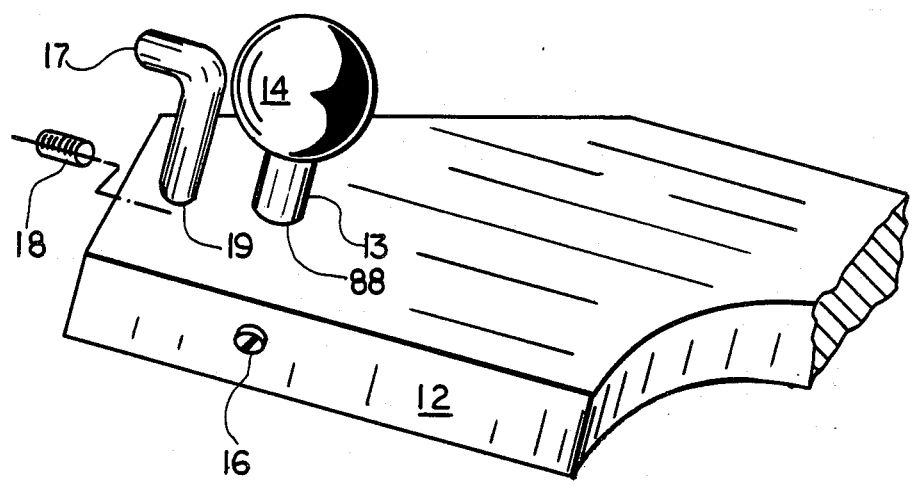
FIG. 2D is an enlarged fragmentary perspective view of an extremity of the mandibular recording assembly shown in FIG. 2A.
Figure 3A:
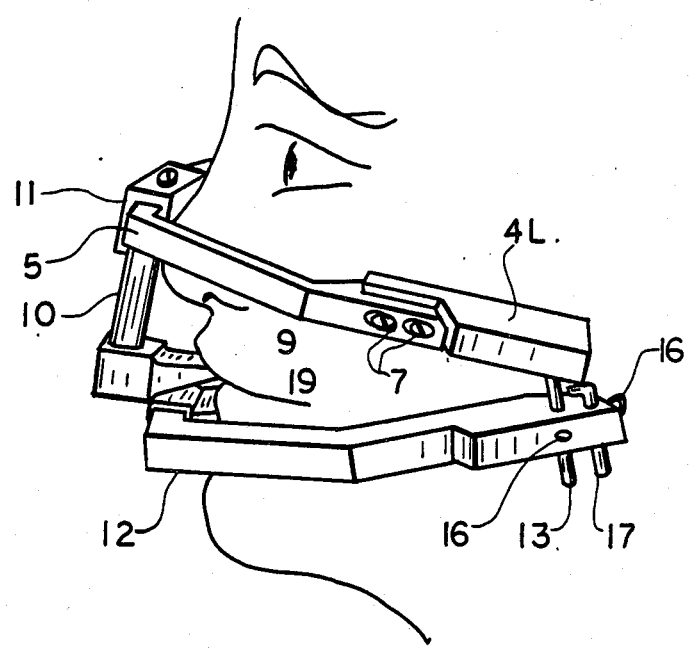
FIG. 3A is a side view of the interengaged maxillary and mandibular recording assemblies illustrating the method of their use.
Figure 3B:
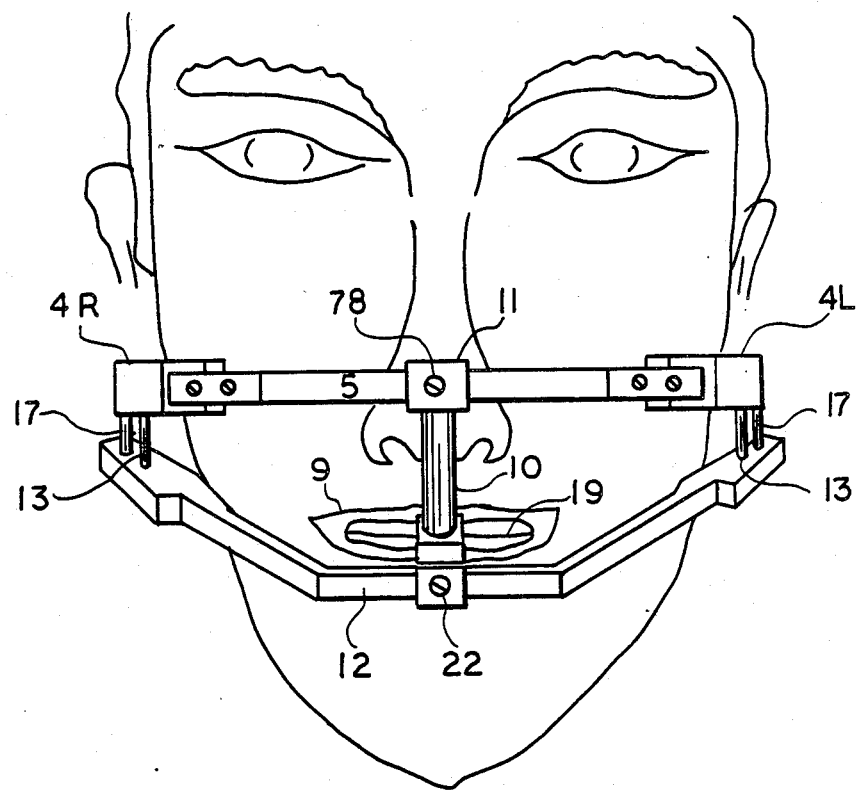
FIG. 3B is a front view of the interengaged recording assemblies of FIG. 3A.
Figure 3C:
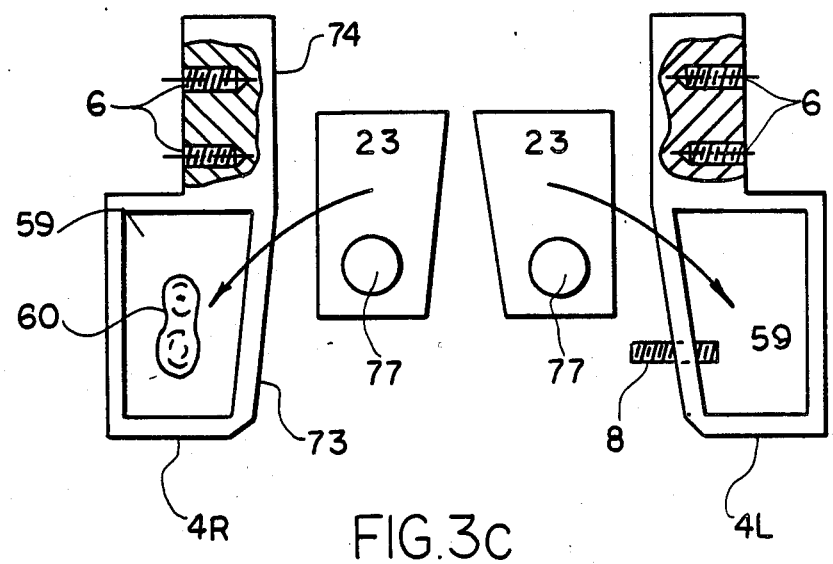
FIG. 3C is an enlarged fragmentary bottom view of the receptacle components of said maxillary recording assembly as shown in FIG. 1B, one of said receptacles being shown containing a condylar pathway, the other receptacle being shown containing an axis orientation pointer.

As shown in FIGS. 3A and 3B, the patient begins molding the condylar pathway, starting from the most retruded mandibular position. The patient is asked to protrude and retrude his lower jaw and subsequently to perform right and left lateral mandibular movements. Such action produces three-dimensional impressions of said motion. The impressions may be added to and lubricated and re-inserted for achieving the most accurate result. After finely detailed, accurate condylar pathways 60, as shown in FIG. 3C, have been established and hardened to constitute stable solid recordings, the maxillary and mandibular recording assemblies are removed from the patient. The aforementioned procedure allows for diagnostic visual observation of the reproduced condylar pathways which yields additional information about the synchrony or asynchrony of the condylar movements as well as the timing of the movement in each condyle for each basic movement. These observations allow the operator to simulate these movements during dental fabrication procedures. This arrangement also allows for three dimensional analysis of condylar pathways.

In the mounting procedure, the patient's maxillary model 61 is seated in the zinc oxide and eugenol paste imprints 62 in maxillary bite plate 9. The base plate 24 of the upper articulator member with attached mounting ring 27 is next secured to the box like receptacles 4R and 4L of the maxillary recording apparatus. This is accomplished utilizing cap screws 31 which penetrate spacers 32 and engage holes 22 in the upper surface 71 of the receptacles. By virtue of such procedure, the maxillary bow is directly transformed into an upper articulator member. The patient's maxillary model is next affixed to the mounting ring 27 of the upper base plate 24 utilizing dental mounting plaster. In such manner of association the teeth of the patient's model 61 seat within the imprint 62 of the upper bite plate 9 and is secured to upper mounting ring 27.

Cap screws 7 are then removed, a procedure which permits removal of first bow 5, with attached upper bite plate which is then set aside. This procedure ensures complete fidelity in the orientation of the patient's maxillary model 61 to the molded condylar pathways 60 and further ensures that the mounted models in the articulator have the same occlusal plane inclination relative to the Frankfort Plane as the patient's jaws have in the head. If methods other than this direct one are used, serious orientation errors could result. The aforesid procedure essentially converts the maxillary recording assembly into an upper articulator member, with the patient's maxillary model 61 mounted and accurately oriented to the molded condylar pathways 60. It is to be noted that the apparatus component heretofore referred to as the upper articulator member is in actuality merely a precursor of the completed member.

Subsequently, the upper articulator member with the mounted maxillary model and condylar pathways is placed on the Teflon balls 14 of the lower articulator member as shown in FIG. 7. Since the medio-lateral distances of the Teflon balls 14 in the mandibular recording apparatus and the Teflon balls in the lower articulator member are identical, the upper condylar pathways fit accurately to the lower Teflon articulator balls which now function as tracing balls. Since the balls are in the most superior position in the clay paths in the centric relation jaw position, the orientation of the balls to this position is very easy and very stable. With upper and lower articulator members in proper interengagement and held in place with elastics over the receptacles containing the condylar pathways, the patient's mandibular model 54 is mounted to the lower articulator member utilizing an interocclusal record 63, as shown in FIG. 7. The assembled articulator by virtue of its specialized features, requires no centric lock for patients with normal condyles. Said interocculusal record is composed of a stiff wax and zinc oxide and eugenol paste and taken in centric relation position. This completes the mounting of the patient's models in proper relationship to the condylar pathways. The assembled articulator is capable of accurately reproducing condylar and mandibular motion in its entire merge as well as opening and closing, without deviation, on the same radius of the arc of closure as a the patient in the retruded condylar position.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. Apparatus for forming a recording of the condylar motion of a dental patient and utilizing said recording for reconstructive purposes as part of a dental articulator, said apparatus comprising:
   (a) a maxillary recording assembly adapted to fit the patient's upper jaw and having: (1) a first rigid U-shaped bow having a straight forward bar and two extremities positioned at equal distances rearwardly of said forward bar, (2) box-like downwardly opening receptacles removably attached to said rearward extremities, and (3) an upper bite plate pendantly attached to said forward bar and displaced rearwardly therefrom, said upper bite plate having a lower abutment surface and an upper surface having a tooth receiving trough,
   (b) a mandibular recording assembly adapted to fit the patient's lower jaw while aligned below said maxillary recording assembly and having: (1) a second rigid U-shaped bow having a straight forward bar and extremities provided with posts perpendicularly adjustable with respect to said bow, (2) a smooth ball affixed to the uppermost extremity of each post and adapted to vertically enter the receptacles of said maxillary recording assembly, and (3) a lower bite plate attached to said forward bar and extending rearwardly therefrom, said lower bite plate having an upper abutment surface and a lower surface having a tooth receiving trough, the relative positioning of said bite plates within said assemblies being such as to permit sliding contact between said abutment surfaces,
   (c) an upper articulator member comprised of a rigid plate having a center zone, and equal left and right side arms radiating from said center zone in a straight line path and terminating in distal extremities having means for attachment of the receptacles of said maxillary recording assembly, and
   (d) a lower articulator member comprised of: (1) a floor plate having rear and forward extremities, (2)

a cross bar positioned above the plate and parallel thereto adjacent said rear extremity, and (3) means for adjustably positioning paired posts above said cross bar, said posts having smooth balls attached to their uppermost extremities, whereby (e) the maxillary and mandibular recording assemblies interact to produce a solid recording confined within said receptacles, and said receptacles can be attached to said upper articulator member in a manner such that said upper articulator member is pivotably supported by vertical interaction with the smooth balls associated with the cross bar of said lower articulator member.

2. Apparatus of claim 1 wherein said upper articulator member is a structural precursor transformable into an upper articulator member by addition of the receptacles of said maxillary recording assembly.

3. Apparatus of claim 1 wherein means slideably associated with the cross bar of said lower articulator member pivotably engages the upper articulator member.

4. Apparatus of claim 1 wherein the rigid plate of said upper articulator member has a forward arm position centered between said left and right side arms, said forward arm holding a vertically adjustable post having a lower extremity which contacts said lower articulator member.

5. A method for forming a recording of the condylar motion of a dental patient and utilizing said recording for reconstructive purposes using a dental articulator having interactive upper and lower members, said method comprising:

(a) having the patient bite down upon slidably abutting bite plates affixed to maxillary and mandibular recording assemblies, one of said assemblies having paired cavities within downwardly opening confining receptacles containing a hardenable plastic composition, the other assembly having paired forming balls which vertically enter said cavities, (b) having the patient execute full mandibular motion while said balls act upon said plastic composition to form paired three-dimensional impressions of said motion, and hardening said composition to form dimensionally stable solid recordings, (c) transferring said recordings to one of the members of a dental articulator in a manner preserving the orientation of said recordings with the patient's teeth, and (d) vertically engaging said recordings by paired stationary tracing balls having the same diameters as said forming balls, said tracing balls being positioned in a manner to preserve the alignment of the patient's maxillary and mandibular teeth.

6. The method of claim 5 wherein the paired cavities containing a hardenable plastic composition are associated with said maxillary recording assembly and are downwardly directed toward said forming balls associated with said mandibular recording assembly.

7. The method of claim 6 wherein said recordings are transferred within said receptacles to the upper member of said dental articulator.

8. The method of claim 7 wherein said transfer is accomplished by first bolting the maxillary recording assembly to a structural precursor of the upper member of the dental articulator, then removing all components of said maxillary recording assembly other than said receptacles, thereby transforming said precursor into the upper member of the dental articulator.

9. The method of claim 8 wherein, prior to the bolting step, the patient's maxillary model is seated within the maxillary bite plate.

10. The method of claim 9 wherein, prior to removal of components of the maxillary recording assembly, the upper extremity of the patient's maxillary model is affixed to said structural precursor.

* * * * *